United States Patent [19]

Rao

[11] Patent Number: 4,680,301
[45] Date of Patent: Jul. 14, 1987

[54] 6-ISOTHIOCYANATO-2,5-SUBSTITUTED BENZOTHIAZOLES OR BENZOXAZOLES USEFUL AS ANTHELMINTIC EFFECTIVE AGENTS

[75] Inventor: Vittal R. Rao, Bombay, India

[73] Assignee: Ciba-Geigy Corporation, Ardsley, N.Y.

[21] Appl. No.: 774,776

[22] Filed: Sep. 11, 1985

[30] Foreign Application Priority Data

Sep. 19, 1984 [GB] United Kingdom ............... 8423697

[51] Int. Cl.⁴ ............... A61K 31/435; C07D 413/04; C07D 417/04
[52] U.S. Cl. ............................. 514/321; 514/183; 514/212; 514/222; 514/237; 514/254; 514/367; 514/375; 544/133; 544/137; 544/368; 546/198; 548/178; 548/217
[58] Field of Search ............... 546/198; 544/133, 137, 544/368; 548/217, 178; 514/183, 212, 222, 237, 321, 254, 367, 375

[56] References Cited

U.S. PATENT DOCUMENTS 3,934,017  1/1976  Gallay et al. .............. 514/367
4,511,567  4/1985  Gallay et al. .............. 514/253

FOREIGN PATENT DOCUMENTS 1123837  5/1982  Canada .............. 514/367

OTHER PUBLICATIONS

Burger, "Medicinal Chemistry", 2nd edition, 1960, p. 42.

Primary Examiner—Donald G. Daus
Assistant Examiner—Cecilia Shen
Attorney, Agent, or Firm—Irving M. Fishman

[57] ABSTRACT

The invention relates to novel benzazole derivatives of the formula I

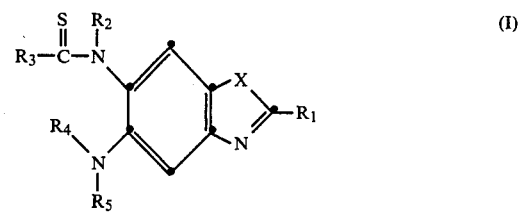

wherein X is oxygen or sulphur, $R_1$ is lower alkyl, lower alkenyl or cycloalkyl, optionally substituted $R_2$ is hydrogen, and $R_3$ is lower alkylthio or lower alkenylthio optionally substituted by esterified hydroxy, carboxy or esterified carboxy or $R_2$ and $R_3$ together are an additional bond of the C-N grouping, and $R_4$ and $R_5$ independently of one another are each hydrogen, lower alkyl or cycloalkyl radicals or taken together are a substituted or unsubstituted bivalent hydrocarbon residue of aliphatic character in which the carbon atoms of the chain may be interrupted by a heteroatom and their salts. The products are useful as anthelmintic effective agents. The products can be prepared according to methods known per se.

12 Claims, No Drawings

6-ISOTHIOCYANATO-2,5-SUBSTITUTED BENZOTHIAZOLES OR BENZOXAZOLES USEFUL AS ANTHELMINTIC EFFECTIVE AGENTS

The invention relates to novel benzazole derivatives of the formula I

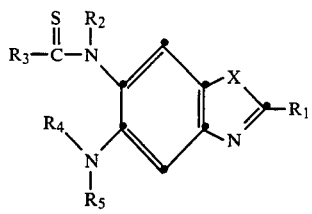

wherein X is oxygen or sulphur, $R_1$ is lower alkyl, lower alkenyl or cycloalkyl, optionally substituted, $R_2$ is hydrogen, and $R_3$ is lower alkylthio or lower alkenylthio optionally substituted by esterified hydroxy, carboxy or esterified carboxy or $R_2$ and $R_3$ together are an additional bond of the C-N grouping, and $R_4$ and $R_5$ independently of one another are each hydrogen, lower alkyl or cycloalkyl radicals or taken together are a substituted or unsubstituted bivalent hydrocarbon residue of aliphatic character in which the carbon atoms of the chain may be interrupted by a heteroatom and their salts and processes for their preparation, pharmaceutical preparations containing them and their use.

The term "lower" used to qualify radicals denotes that these contain up to 7 carbon atoms preferably up to 4 carbon atoms. Lower alkyl and alkenyl radicals may be straight-chain or branched-chain radicals substituted by free, esterified or etherified hydroxy groups, such as lower alkanoyloxy, lower alkoxy or lower alkenyloxy groups or halogen atoms, and also free or esterified carboxyl groups, such as lower alkoxycarbonyl, as for example methoxy- or ethoxycarbonyl, or lower alkylthio such as methylthio, ethylthio, n-propylthio, isopropyl or n-butylthio and lower alkenylthio such as allyl- or 2-methylallylthio groups.

Halogen atoms are in particular fluorine, chlorine or bromine atoms, but can also be iodine atoms.

Lower alkyl groups are, for example, preferably methyl groups and also ethyl, n-propyl, isopropyl, n-butyl, isobutyl, sec-butyl, tert.-butyl. Lower alkenyl groups are, for example the allyl group or the 2-methylallyl group. Substituted lower alkyl groups are for example, the trifluoromethyl group or a free or esterified carboxymethyl groups, for example the methoxycarbonylmethyl group.

Lower alkoxy is, for example, methoxy, ethoxy, n-propoxy, isopropoxy, n-butoxy or n-pentyloxy and lower alkenyloxy is, for example, vinyloxy or allyloxy.

A cycloalkyl group is primarily a monocyclic residue having for example 3 to 10 carbon atoms preferably 5 to 7 carbon atoms, for example, a cyclopentyl, cyclohexyl and cycloheptyl group.

The groups $R_4$ and $R_5$ when they represent an optionally substituted bivalent hydrocarbon residue of aliphatic character is a group such as lower alkylene which contains between 4 and 7 carbon atoms in the chain. The substituents on the bivalent hydrocarbon may be one or more lower alkyl groups or an optionally substituted phenyl radical. Thus the substituted bivalent hydrocarbon radical together with the nitrogen atom as lower alkyleneamino represents a heterocyclic radical such as pyrrolidino, piperidino, 2-methyl, 4-methyl or 4-phenyl piperidino, hexahydroazepino or octahydroazocino group. The bivalent hydrocarbon chain as such may be interrupted by a hetero atom, for example oxygen, sulphur, substituted or unsubstituted nitrogen representing as oxa-lower alkylene amino, morpholino, 2,6-dimethylmorpholino or as thia-lower alkylene amino for example thiamorpholino, or optionally substituted aza-lower alkylene amino for example piperazino, for example N-methyl-, N-phenyl-, N-acetyl-, N-methoxycarbonyl-, N-ethoxycarbonyl-, or N-methanesulphonyl-piperazino. Substituents on the optionally substituted nitrogen atom which interrupt the bivalent hydrocarbon chain in case of an optionally substituted piperazino group may be an optionally substituted lower alkyl group or an aryl group, such as phenyl an acyl group such as lower alkanoyl, e.g. acetyl or aroyl e.g. benzoyl, or a lower alkoxycarbonyl group, such as ethoxycarbonyl or methoxycarbonyl or lower alkane sulphonyl group, e.g. methane sulphonyl group.

The benzene nucleus may be optionally substituted by lower alkyl, alkoxy, or alkoxycarbonyl groups or halogen atoms.

The novel compounds have valuable pharmacological properties. They are useful in the control of parasitic helminths such as nematodes, cestodes and trematodes. They are particularly useful in the control of pathogens in filariasis such as *Litomosoides carinii, Brugia malayi, Brugia pahangi* and *Dipetalonema viteae* and of their development stages. In the treatment of filariasis in multimammate rat (*Mastomys natalensis*) and jirds (*Meriones unguiculatus*). The new compounds have proved to be very potent as macro and microfilaricides on administration orally 2–5 times of a dose of 5 to 25 mg/kg.

The invention relates preferred to compounds of formula I, wherein X is oxygen or sulphur, $R_1$ is lower alkyl or lower alkenyl, $R_2$ is hydrogen, and $R_3$ is lower alkylthio optionally substituted by carboxy or esterified carboxy, or $R_2$ and $R_3$ together are an additional bond of the C-N grouping, and $R_4$ and $R_5$ are hydrogen or lower alkyl or taken together represent a substituted or unsubstituted lower alkylene optionally interrupted by oxygen, sulphur or optionally substituted nitrogen with a total of 4 to 6 carbon atoms in the chain and their salts.

Particularly of interest are compounds of the formula I wherein X is sulphur, $R_1$ is lower alkyl, $R_2$ is hydrogen and $R_3$ is a carboxy lower alkyl mercapto group or $R_2$ and $R_3$ taken together are an additional bond of the C-N grouping and $R_4$ and $R_5$ are hydrogen, lower alkyl or together represent lower alkylene with a total of 4 or 5 carbon atoms in the chain optionally interrupted by oxygen, sulphur or nitrogen where nitrogen is optionally substituted by lower alkyl, lower alkanoyl, lower alkoxycarbonyl, lower alkane sulphonyl or phenyl, and their salts.

Of particular interest are compounds of the formula Ia

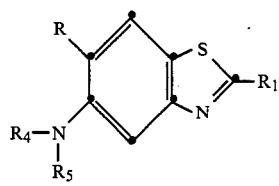

wherein R is NCS or a

group and $R_1$ is lower alkyl with 3 and 4 carbon atoms and $R_4$ and $R_5$ are hydrogen, lower alkyl or together with the nitrogen atom represent lower alkyleneamino with 4 or 5 carbon atoms in the chain optionally interrupted by oxygen, sulphur or nitrogen, optionally substituted by lower alkyl, lower alkanoyl, lower alkoxycarbonyl, lower alkane sulphonyl or phenyl and their pharmaceutically acceptable salts.

The most preferred compounds of formula Ia are compounds wherein R is NCS or a

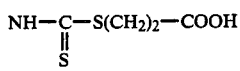

group, $R_1$ is tert.butyl and $R_4$ and $R_5$ is lower alkyl such as methyl or together with the nitrogen atom as lower alkyleneamino are a heterocyclic radical, such as pyrrolidyl, piperidyl, morpholinyl, piperazinyl, or methylpiperazinyl, phenyl-piperazinyl, acetyl-piperazinyl, methanesulphonyl-piperazinyl, methoxycarbonyl- or ethoxycarbonyl-piperazinyl and their pharmaceutically acceptable salts.

The invention relates especially to compounds of the formula I mentioned in the examples and their salts.

The novel benzazoles of the formula I are obtained by methods known per se.

Isothiacyano benzazole compounds of formula I wherein $R_2$ and $R_3$ taken together constitute an additional bond of the C-N grouping can be obtained by several processes.

The first process involves treatment of compounds of formula II

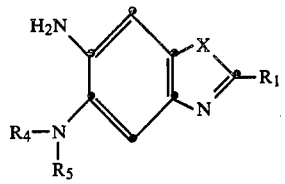

wherein X, $R_1$, $R_4$ and $R_5$ are as defined under formula I with thiophosgene in an inert solvent.

According to a second process isothiocyanobenzazoles compounds of formula I can be obtained by pyrolysis of compounds of formula III

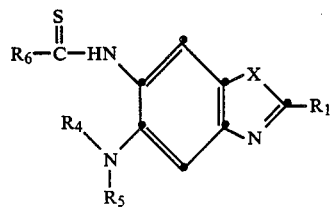

wherein X, $R_1$, $R_4$ and $R_5$ are as defined under formula I and $R_6$ is a group detachable by pyrolysis, preferably amino, lower alkylthio or the thioammonium group

In a typical reaction for the process the pyrolysis is for example carried out in high boiling solvents, e.g. in refluxing chlorobenzene.

As a variant of the above process, an oxidizing pyrolysis, is carried out for example by oxidation of compounds of the formula III, wherein $R_6$ is a thioammonium groups

wherein X, $R_1$, $R_4$ and $R_5$ have the meanings defined above. The oxidation is carried out for example by oxidising agents, such as lead nitrate or sodium hypochlorite.

Isothiocyanobenzazoles of formula I are also obtained by a third process by treating compounds of the formula IV

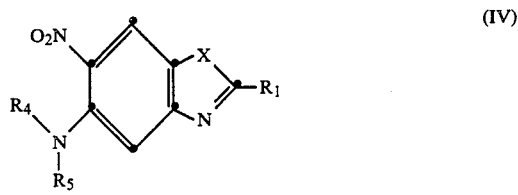

wherein X, $R_1$, $R_4$ and $R_5$ have the meanings defined above with carbon disulphide, preferably in presence of sodium hydroxide in an autoclave as described in literature. (G. Ottmann and E. Kober. *Angew. Chem. Int. Ed.* 8 780 (1969).

In a fourth process, isothiocyano benzazoles of formula I are obtained by thermal isomerisation of V

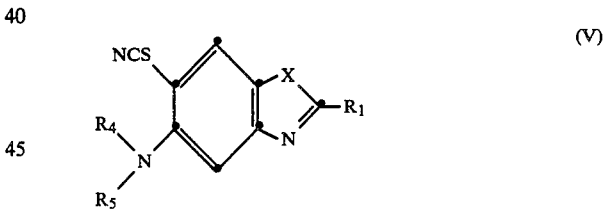

where X, $R_1$, $R_4$ and $R_5$ have the meanings defined as above, in high boiling solvents.

The resulting compounds of formula I wherein $R_2$ and $R_3$ taken together constitute an additional bond of the C-N grouping are converted into compounds of formula I wherein $R_2$ is hydrogen and $R_3$ is for example carboxy alkyl mercapto group by conventional methods. Thus benzazole dithiocarbamates of formula I wherein $R_2$ is hydrogen and $R_3$ is lower alkylthio are obtained by treating isothiocyanobenzazoles of formula I with ω-mercaptoalkane derivatives of formula VI

wherein n is an integer 2 or 3 and R is a carboxy group, lower alkoxycarbonyl or lower alkoxy group.

Benzazoledithiocarbamates of formula I are also obtained from compounds of formula II described above with carbondisulphide in presence of an alkalimetal followed by treatment with ω-halogenoalkyl acids, esters or ethers, such as an ω-bromoalkyl acids, esters or ethers.

The processes described can be carried out in the conventional manner at ambient temperature, with cooling or warming, under normal pressure or elevated pressure and, if necessary, in the presence or absence of a diluent, catalyst or condensing agent. If necessary, the reaction can also be carried out in the atmosphere of an inert gas, for example, nitrogen.

In resulting compounds substituents can be introduced, modified or detached within the scope of the definition of the end products.

Depending on the process conditions and the starting materials the end products are obtained in the free form or in the form of their salts, especially acid addition salts which are also included in the invention. The acid addition salts of the novel compounds can be converted to the free compound in a manner per se, for example with basic agents such as alkali or ion exchangers. On the other hand the resulting free bases can form salts with organic or inorganic acids. Acids used to prepare acid addition salts are in particular those which are suitable for forming therapeutically usable salts.

The following may be mentioned as examples of suitable acids: hydrohalic acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycolic acid, latic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicyclic acid, embonic acid, methanesulfonic acid, ethanesulfonic acid, hydroxyethanesulfonic acid, or ethylenesulfonic acid; halogenobenzenesulfonic acid, toluenesulfonic acid, naphthalenesulfonic acid or sulfanilic acid; and methionine, tripthophane, lysine or arginine.

These or other salts of the novel compounds, for example the picrates, can also be used to purify the free bases obtained, the process comprising converting the free bases into salts, separating these, and liberating the bases.

The invention also relates to these embodiments of a process in which a process is discontinued at any stage or in which a compound obtainable as an intermediate at any stage is used as the starting material and the missing process steps are carried out, or a starting material is formed under the reaction conditions, or if desired, is used in the form of a salt. The invention also includes novel intermediates resulting therefrom. The starting materials are known or if they are novel, can be prepared by methods known per se.

Starting compounds of formula II can be prepared by a sequence of reactions starting from 2,5-dichloroaniline. Acylation with an alkanecarboxylic chloride yields the amide which on nitration followed by treatment with phosphorous pentasulfide yields the thioamide VIII

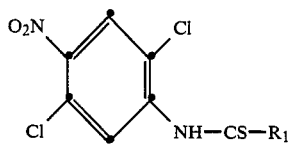

(VIII)

wherein $R_1$ has the meaning defined under I.

Treatment with triethylamine in dimethyl sulfoxide followed by reaction with acylic or cyclic secondary amines yields a compound of the formula IX

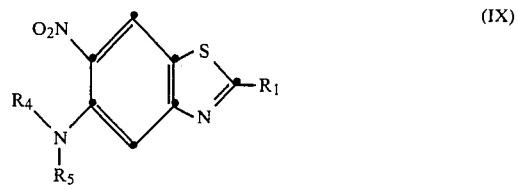

(IX)

wherein $R_1$, $R_4$ and $R_5$ have the meanings defined under I. IX may also be obtained in one step from VIII by the use of excess of the acyclic or cyclic secondary amine in dimethyl sulfoxide in the presence of potassium carbonate. The reduction of the aromatic nitro compound of the formula IX to II is effected in a manner known per se by hydrogenation in presence of Raney Nickel or a palladium on charcoal catalyst in a suitable solvent. This reduction can also be carried out by known chemical routes, for example using metals, for example, zinc or iron in the presence of mineral acids or alkane carboxylic acids such as acetic acid.

The starting compounds of the formula III used in the second process can be obtained from compounds of the formula II by conventional methods. For example compounds of formula III, wherein $R_6$ is a thioammonium group, by reacting a compound of formula II with ammoniumthiocyanate in the presence of concentrated sulphuric acid under reflux temperature.

The starting compounds of formula V can be obtained by thiocyanation, of compounds of formula X

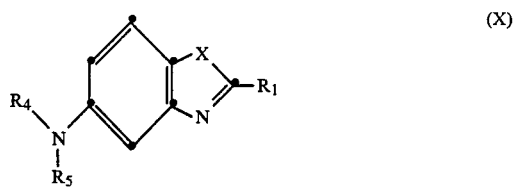

(X)

wherein X, $R_1$, $R_4$ and $R_5$ have the meanings defined above, prepared according to methods described in literature. (E.D. Sync. Ukrain. Khim. Zhur, 25, 767–73. (1958) C.A.54 13144.

Evaluation in the animal test systems mentioned above show the excellent potential of the novel compounds as micro and macrofilaricides, for example, for lymphatic filariasis, orchocerciasis and schistosomiasis for which an effective dosage ranging from 5 to 50 mg/kg daily by oral administration over a period of one to 5 days is to be used.

The pharmaceutical preparations according to the invention, which contain compounds of the formula I or pharmaceutically acceptable salts thereof, are those for enteral, such as oral or rectal, and parenteral, administration to warm-blooded animals, that contain the pharmacological active substance alone or together with a pharmaceutically acceptable carrier. The dosage of the active substance depends on the species of warm-blooded animal, the age and the individual condition, and on the method of administration.

The new pharmaceutical preparations contain, for example, from approximately 10% to approximately 90%, preferably from approximately 20% to approximately 60%, of the active substance. Pharmaceutical preparations according to the invention for enteral or parenteral administration are, for example, those in dosage unit forms, such as dragees, tablets, capsules or suppositories, or also ampoules. These are produced in a manner known per se, for example by means of conventional mixing, granulating, coating, dissolving or lyophilising processes. Thus, pharmaceutical preparations for oral administration can be obtained by combining the active substance with solid carriers, optionally granulating a resulting mixture, and processing the mixture or granulate to form tablets or dragee cores, if desired or necessary after the addition of suitable adjuncts.

Suitable carriers are especially fillers, such as sugars, for example lactol or sorbitol, cellulose preparations and/or calcium phosphates, for example tricalcium phosphate or calcium hydrogen phosphate, also binders, such as starch pastes using, for example, corn, wheat, rice or potato starch, gelatin, tragacanth, methylcellulose and/or polyvinylpyrrolidone, and/or, if desired, disintegrators, such as the above-mentioned starches, and also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragee cores are provided with suitable, optionally gastric juice-resistant coatings, there being used, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, to produce gastric juice-resistant coatings, solutions of suitable cellulose preparations, such as acetylcellulose phthalate or hydroxypropylmethylcellulose phthalate. Colouring matter or pigments may be added to the tablets or dragee coatings, for example for identification purposes or for indicating different doses of active substance.

Other pharmaceutical preparations for oral administration are dry-filled capsules made of gelatin and soft sealed capsules consisting of gelatin and a plasticiser, such as glycerin or sorbitol. The dryfilled capsules may contain the active substance in the form of a granulate, for example in admixture with fillers, such as lactose, binders, such as starches, and/or glidants, such as talc or magnesium stearate, and optionally, stabilisers. In soft capsules the active substance is preferably dissolved or suspended in suitable liquids, such as fatty oils, paraffin oil or liquid polyethylene glycols, it likewise being possible for stabilisers to be added.

These come into consideration as rectally administerable pharmaceutical preparations, for example suppositories consisting of a combination of the active substance with a suppository base. Suitable suppository bases are, for example, natural or synthetic triglycerides, paraffin hydrocarbons, polyethylene glycols or higher alkanols. It is also possible to use gelatin rectal capsules that contain combination of the active substance with a base substances, for example liquid triglycerides, polyethylene glycols or parrafin hydrocarbons.

Especially suitable forms for parenteral administration are aqueous solutions of an active substance in water-soluble form, for example a water-soluble salt, or suspensions of the active substance, such as corresponding oily injection suspensions, suitable lipophilic solvents or vehicles, such as fatty oils, for example sesame oil, or synthetic fatty acid esters, for example ethyl oleate or triglycerides, being used, or aqueous injection suspensions that contain viscosity-increasing substances, for example sodium carboxymethylcellulose, sorbitol and/or dextran and optionally also stabiliseres.

Tinctures and solutions usually have an aqueous ethanolic base, to which there are added inter alia, polyalcohols, for example glycerin, glycols and/or polyethylene glycol, as moisture-retaining agents for reducing evaporation, and fat-restoring substances, such as fatty acid esters with low polyethylene glycols, that is to say lipophilic substances soluble in aqueous mixture as a replacement for the fatty substances removed from the skin by the alcohol, and if necessary, other adjuncts and additives.

The present invention relates also to the use of the compounds of the formula I and the salts of such compounds with salt-forming properties, preferably for combating parasitising helminths, especially those of the families mentioned above.

The following Examples illustrate the above-described invention but are in no way intended to limit the scope thereof. Temperatures are in degrees Centigrade.

EXAMPLE 1

A mixture of 100 g of N-[2-tert-butyl-5-(piperidin-1-yl)]benzothiazol-6-yl thiourea and 18 g of ammonium sulphate in 3000 ml of dry chlorobenzene is refluxed for 8 hrs and the ammonium produced in the reaction is swept off by a current of nitrogen gas. After cooling, the solvent is removed from the reaction mixture and extracted with hexane. The hexane extract is filtered through a bed of 200 g of silica gel and the filtrate is evaporated to yield 2-tert-butyl-6-isothiocyanato-5-(piperidin-1-yl)benzothiazole

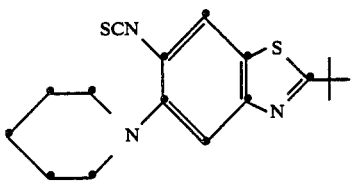

melting at 112°–114° C.

The starting material for the above synthesis is prepared as follows:

To a stirred solution of 1 kg of 2,5-dichloroaniline in 2500 ml of pyridine is added 840 ml of pivaloyl chloride and the mixture is refluxed for 4 hours. After cooling, the reaction mixture is poured into water. The solid is filtered, washed with water and air dried to yield N-tert-butylcarbonyl-2,5-dichloroaniline, melting at 74°–76°.

To a stirred mixture of 369 g of the above compound in 1800 ml of conc. sulphuric acid at −2° is added a mixture of 465 ml of conc. nitric acid and 230 ml of water over 1.5 hours. The mixture is further stirred for 0.5 hour at −2° and poured into ice-water. The solid is filtered off, suspended in water and treated with dilute sodium bicarbonate till the pH is 7. The solid is then filtered, washed with water and cold alcohol to yield N-tert-butylcarbonyl 2,5-dichloro-4-nitroaniline, melting at 142°–145°.

A mixture of 300 g of the above compound and 360 g of phosphorous pentasulphide in 2500 ml of acetonitrile is refluxed with stirring for 15 hours, cooled and filtered. The filtrate is evaporated to dryness and the residue crystallised from alcohol to yield N-tert-butyl-thiocarbonyl-2,5-dichloro-4-nitroaniline, melting at 142°–144°.

A stirred mixture of 462 g of the above compound, 421 g of anhydrous potassium carbonate and 225 ml of piperidine in 1200 ml of dimethyl sulphoxide is heated at 150° for 10 hours, cooled and poured into water. The solid is filtered, washed with water and isopropyl alcohol to yield 2-tert-butyl-6-nitro-5-(piperidin-1-yl)benzothiazole, melting at 147°–148°.

To a vigorously stirred suspension of 560 g activated iron in 500 ml of distilled water containing 66 ml of acetic acid at 100° is added under nitrogen, 252 g of the above compound portion-wise, and the mixture refluxed for 10 hours. After cooling the mixture is filtered and the solid extracted with ethyl acetate. The etyhl acetate extract is concentrated, treated with hexane to yield 6-amino-2-tert-butyl-5-(piperidin-1-yl)benzothiazole, melting at 172°–175°.

A stirred mixture of 288 g of the above compound and 150 g of dry ammonium thiocyanate in 1500 ml of isopropyl alcohol is heated to 60° under nitrogen and 100 g of conc. sulphuric acid is added dropwise. After the addition of sulphuric acid the mixture is refluxed for 12 hours, cooled and pured into water. The suspension is treated with 10% sodium hydroxide solution till pH is 8. The solid is filtered, washed with water and methanol to yield N-[2-tert-butyl-5-(piperidin-1-yl)-benzothiazol-6-yl]thiourea, melting at 228°–232°.

EXAMPLE 2

A solution of 1 g of 2-tert-butyl-6-isothiocyanato-5-(piperidin-1-yl)benzothiazole, described in Example 1 and 0.5 g of 3-mercaptopropionic acid in 20 ml of N,N-dimethylformamide is stirred at ambient temperature under nitrogen for 24 hours. The solution is poured into water, the solid filtered, washed with water and crystallised from acetonitrile to yield 2-tert-butyl-6-N-[($\beta$-carboxyethylthio)thiocarbonyl]amino-5-(piperidin-1-yl)benzothiazole, melting at 158°.

EXAMPLE 3

To a stirred mixture of 75 g of 6-amino-2-tert-butyl-5-(4-methylpiperazin-1-yl)benzothiazole and 29 g of sodium bicarbonate in 1100 ml of chloroform at 0° is added 41 g of thiophosgene and the mixture stirred at 10° for 4 hours. After filtering off the solid, the solution is evaporated to get an yellow solid which is dissolved in water and the pH of the solution is brought to 7 by the addition of dilute sodium hydroxide. The solid separated is extracted with hexane and filtered through 150 g of neutral alumina to give 2-tert-butyl-6-isocyanato-5-[4-methyl-piperazin-1-yl]benzothiazole melting at 124°–126°.

The starting material for the above compound is prepared as follows:

A solution of 171 g of N-t-butylthiocarbonyl-2,5-dichloro-4-nitroaniline, described in Example 1, and 605 ml of N-methylpiperazine in 1700 ml of dimethylsulphoxide is heated at 140° for 8 hours, cooled and poured into water. The solid is filtered, washed with water and cold isopropanol to yield 2-tert-butyl-5-[4-methylpiperazin-1-yl]-6-nitrobenzothiazole, melting at 132°–135°.

A solution of 86 g of the above compound in 150 ml of ethanol is hydrogenated in presence of 30 g Raney Nickel at 45° C. The solution is filtered to remove the catalyst, concentrated and the solid filtered to give 6-amino-2-tert-butyl-5-[4-methylpiperazin-1-yl]benzothiazole, melting at 130°.

EXAMPLE 4

A solution of 0.5 g 2-tert-butyl-6-isothiocyanato-5-[4-methylpiperazin-1-yl]benzothiazole described in Example 3, and 0.25 g of 3-mercaptopropionic acid in 5 ml of dimethylformamide is stirred in nitrogen atmosphere for 24 hours. The solvent is removed under vacuum and the solid obtained is crystallised from acetonitrile to yield 2-tert-butyl-6-N-[($\beta$-carboxyethylthio)thiocarbonyl]-amino-5-(4-methylpiperazin-1-yl)benzothiazole, melting at 167°–170°.

EXAMPLE 5

A mixture of 2.3 g of N-2-tert-butyl-5-[pyrrolidin-1-yl-benzothiazole-6-yl]thiourea and a pinch of ammonium sulphate in 100 ml of chlorobenzene is refluxed for 6 hours in a current of nitrogen. Chlorobenzene is removed under vacuum and the residue is dissolved in hexane and filtered through silica gel and the filtrate is evaporated to yield 2-tert-butyl-6-isothiocyanato-5-[pyrrolidin-1-yl]benzothiazole, melting at 89°–90°.

The starting material for the above compound is prepared as follows:

A mixture of 94 g of N-tert-butylthiocarbonyl-2,5-dichloro-4-nitroaniline, described in Example 1, in 360 ml of dimethylsulphoxide and 160 ml of triethylamine is heated at 140° for 10 hours under nitrogen. The reaction mixture is cooled and poured into water. The solid obtained is filtered and washed with water and air-dried to yield 2-tert-butyl-5-chloro-6-nitrobenzothiazole, melting at 65°–69°.

A solution of 7 g of the above compound in 15 ml of pyrrolidine is refluxed for 10 hours. The reaction mixture is evaporated under reduced pressure and the residue boiled with alcohol and cooled to give 2-tert-butyl-6-nitro-5-[pyrrolidin-1-yl]benzothiazole, melting at 115°–117°.

A solution of 6 g of the above compound in 300 ml of methanol is hydrogenated in presence of 3 g of Raney Nickel. The catalyst is filtered off, the solution concentrated and the solid filtered to yield 6-amino-2-tert-butyl-5-[pyrrolidin-1-yl]benzothiazole, melting at 130°–132°.

A mixture of 4.8 g of the above compound and 4 g of ammonium thiocyanate in 20 ml of isopropyl alcohol is heated to 60° under nitrogen and 2.5 g of concentrated sulphuric acid is added dropwise.

The reaction mixture is refluxed for 7 hours, cooled, made strongly basic with aqueous sodium hydroxide and filtered. The solid is washed with water and then with methanol to yield N-[2-tert-butyl-5-(pyrrolidin-1-yl)benzothiazole-6-yl]thiourea melting at 221°.

EXAMPLE 6

To a cooled mixture of 143 g of 6-amino-2-tert-butyl-5-morpholinobenzothiazole and 168 g of sodium bicarbonate in 200 ml of $CHCl_3$ is added 75 g of thiophosgene under stirring. The stirring is continued at ambient temperature for 10 hours. The solide are filtered off and the filtrate is evaporated. The solid thus obtained is dissolved in hexane and filtered through a silica gel column. The filtrate is evaporated to give 2-tert-butyl-6- isothiocyanato-5-[morpholin-4-yl]benzothiazole melting at 141°–143°.

The starting material is prepared as follows:

A solution of 170 g of 2-tert-butyl-5-chloro-6-nitrobenzothiazole described in Example 5, in 200 ml of morpholine is refluxed for 6.5 hours, cooled and poured into water. The solid is filtered, washed with water and cold alcohol to give 2-tert-butyl-5-[morpholin-4-yl]-6-nitrobenzothiazole melting at 119°–121°.

A solution of 173 g of 2-tert-butyl-5-[morpholin-4-yl]-6-nitrobenzothiazole in 5000 ml of methanol is hydrogenated in presence of 40 g of Raney Nickel at room temperature. After removing the catalyst the solution is concentrated and the solid filtered to give 6-amino-2-tert-butyl-5-morpholinobenzothiazole, melting at 158°–159°.

EXAMPLE 7

A mixture of 100 g of 2-tert-butyl-6-isothiocyanato-5-[morpholino-4-yl]benzothiazole described in Example 6 and 62.4 g of 3-mercapto propionic acid in 700 ml of N,N-dimethylformamide is stirred under nitrogen for 15 hours. The clear solution is poured into water, the solid obtained is filtered, washed with water and air dried. The solid is crystallised from ethyl acetate to give 2-tert-butyl-6-N-[(β-carboxyethylthio)thiocarbonyl]-amino-5-(morpholin-4-yl)benzothiazole, melting at 180.5°–182.5°.

EXAMPLE 8

To a mixture of 2 g of 6-amino-2-tert-butyl-5-[thiomorpholin-4-yl]benzothiazole and 2 g of anhydrous potassium carbonate in 150 ml of chloroform at 0° is added 0.6 ml of thiophosgene in 5 ml chloroform, under stirring. After 4 hours of stirring at ambient temperature the mixture is filtered. The filtrate is evaporated to a solid which is purified by silica gel column chromatography. The column is eluted with hexane/methylenechloride (1:1) to give 2-tert-butyl-6-isothiocyanato-5-[thiomorpholin-4-yl]benzothiazole, melting at 155°–159°.

The starting material for the above compound is prepared as follows:

A mixture of 2 g of 2-tert-butyl-5-chloro-6-nitrobenzothiazole, described in Example 5, 2 g of anhydrous potassium carbonate and 1.5 ml of thiomorpholine in 7 ml of 1-methyl-2-pyrrolidinone is heated in a sealed glass tube at 120° for 12 hours, poured into water, the solid filtered, washed with water and isopropyl alcohol to give 2-tert-butyl-6-nitro-5-[thiomorpholin-4-yl]benzothiazole, melting at 117°–120°.

A solution of 4.2 g of the above compound in 150 ml of methanol is hydrogenated in the presence of 2.5 g of Raney Nickel at 45°. After removing, the solution is concentrated, the solid filtered and washed with cold methanol to give 6-amino-2-tert-butyl-5-[thiomorpholin-4-yl]benzothiazole, melting at 170°–175°.

EXAMPLE 9

A mixture of 2 g of 6-amino-2-tert-butyl-5-[4-phenylpiperazin-1-yl]benzothiazole and 2 g of anhydrous potassium carbonate in 150 ml of chloroform is treated with 4 ml of thiophosgene at 0° C. The mixture is stirred at room temperature for 3 hours and then stirred with 10% NaOH for 5 minutes. The organic layer is separated, dried and evaporated to give an oil, which is applied on silica gel column and eluted with 1% methanol in chloroform to give 2-tert-butyl-6-isothiocyanato-5-[4-phenylpiperazin-1-yl]benzothioazole, melting at 120°–123°.

The starting material for the above compound is prepared as follows:

A mixture of 7 g of 2-tert-butyl-5-chloro-6-nitrobenzothiazole described in Example 5, in 8.2 g of N-phenylpiperazine is heated at 150°–160° for 12 hours, cooled and poured into water. The paste is extracted with methylene chloride, washed with 2N HCl, then with 10% NaOH and then with water. The organic layer is dried, the solvent evaporated and the solid crystallised from isopropyl alcohol to give 2-tert-butyl-6-nitro-5-[4-phenylpiperazin-1-yl]benzothiazole, melting at 152°–155°.

A solution of 4.7 g of the above compound in 150 ml of methanol is hydrogenated in the presence of 2.5 g of Raney Nickel at ambient temperature. After filtering off the catalyst, the solution is evaporated and the solid crystallised from ether to give 6-amino-2-tert-butyl-5-[4-phenylpiperazin-1-yl]benzothiazole, melting at 129°–132°.

EXAMPLE 10

A mixture of 2 g of 6-amino-2-tert-butyl-5[4-carbethoxypiperazin-1-yl]benzothiazole and 2 g of sodium bicarbonate in 200 ml of chloroform is cooled in an ice bath and 4 ml of thiophosgene in 10 ml of chloroform is added and the mixture is stirred at ambient temperature for 2 hours. The solid is filtered off and the filtrate is evaporated to give an oil which is applied on a silica gel column with 1% methanol in chloroform to yield 2-tert-butyl-5-[4-carbethoxypiperazin-1-yl]-6-isothiocyanatobenzothiazole, melting at 131°–134°.

The starting material for the above compound is prepared as follows:

A mixture of 3.5 g of 2-tert.-butyl-5-chloro-6-nitrobenzothiazole, described in Example 5, and 5.8 g of N-carbethoxypiperazine is heated at 180° for 2 hours, cooled and poured into water. The solid is filtered, washed with water and crystallised from isopropyl alcohol to give 2-tert-butyl-5-[4-carbethoxypiperazin-1-yl]-6-nitrobenzothiazole, melting at 100°–102°.

A solution of 4.4 g of the above compound in 150 ml of methanol is hydrogenated in the presence of 3 g of Raney Nickel at 45° C. The catalyst is filtered off and the solution concentrated. The solid obtained is filtered to give 6-amino-2-tert-butyl-5-[4-carbethoxypiperazin-1-yl]benzothiazole, melting at 215°–220°.

EXAMPLE 11

A mixture of 2 g of 6-amino-2-tert-butyl-5-[4-acetylpiperazin-1-yl]benzothiazole and 1.5 g of sodium bicarbonate in 150 ml of chloroform is cooled to 0° and 4 ml of thiophosgene is added dropwise and stirred at ambient temperature overnight. The solid is filtered off and the filtrate is evaporated under reduced pressure. The oil so obtained is applied on a silica gel column and eluted with 1% methanol in chloroform to yield 2-tert-butyl-6-isothiocyanato-5-[4-acetylpiperazin-1-yl]benzothiazole, melting at 100°–102°.

The starting material for the above compound is prepared as follows:

A solution of 13.5 g of 2-tert-butyl-5-chloro-6-nitrobenzothiazole described in Example 5, and 40 g of anhydrous piperazine in 100 ml of dimethylsulphoxide is heated at 140° for 2 hours, cooled and poured into ice-water. The yellow solid is filtered, washed with water and dried at 80° to yield 2-tert-butyl-6-nitro-5-[piperazin-1-yl]benzothiazole, melting at 144°-146°.

A mixture of 5 g of the above compound and 4 ml of acetic anhydride in 8 ml of glacial acetic acid is refluxed for 2 hours, cooled and poured into water. The solid is filtered, washed with water and crystallised from alcohol to yield 5-[4-acetylpiperazin-1-yl]-2-tert-butyl-6-nitrobenzothiazole, melting at 166°-168°.

A solution of 3 g of the above compound in 150 ml of methanol is hydrogenated in presence of 2 g of Raney Nickel. After removing the catalyst, the solution is concentrated and the solid filtered to give 5-[4-acetyl-piperazin-1-yl]-6-amino-2-tert-butyl-benzothiazole, melting at 182°-185°.

EXAMPLE 12

A mixture of 1 g of 6-amino-2-tert-butyl-5-[4-methanesulphonylpiperazin-1-yl]benzothiazole and 500 g of sodium bicarbonate in 100 ml of chloroform is cooled in an ice-bath and 2 ml of thiophosgene in 10 ml of chloroform is added to it under stirring. The mixture is stirred over-night at ambient temperature. After filtering off the solid the filtrate is evaporated and the residue is subjected to silica gel column chromatography. Elution with 1% methanol in chloroform gives 2-tert-butyl-6-isothiocyanato-5-[4-methanesulphonyl-piperazin-1-yl]benzothiazole melting at 128°-130°.

The starting material for the above compound is prepared as follows:

To a solution of 5 g of 2-tert-butyl-6-nitro-5-[piperazin-1-yl]benzothiazole, described in Example 11, in 25 ml of pyridine is added 2.3 g of methanesulfphonyl chloride and the mixture is heated at 90° for 10 min. The mixture is cooled, poured into water, the solid filtered, washed with water and then with isopropyl alcohol to give 2-tert-butyl-6-nitro-5-[4-methanesulphonyl-piperazin-1-yl]benzothiazole, melting at 195°-197°.

A solution of 5 g of the above compound in 500 ml of methanol is hydrogenated in the presence of 3 g of Raney Nickel at 40°. After filtering off the catalyst the solution is concentrated, the solid filtered and washed with hexane to give 6-amino-2-tert-butyl-5-[4-methanesulphonylpiperazin-1-yl]benzothiazole melting at 153°-155°.

EXAMPLE 13

A mixture of 1.5 g of N-[(2-tert-butyl-5-N,N-dimethylamino)benzothiazol-6-yl]thiourea and 0.4 g of ammonium sulphate in 160 ml of chlorobenzene is refluxed under nitrogen for 12 hours and the solvent removed under vacuum. The solid is extracted with hexane and filtered through silica gel column to give 2-tert-butyl-5-[N,N-dimethyl]amino-6-isothiocyanatobenzothiazole, melting at 63°-66°.

The starting material for the above compound is prepared as follows:

A solution of 16.2 g of 2-tert-butyl-5-chloro-6-nitrobenzothiazole, described in Example 5, in 150 ml hexamethyl phosphoric triamide is heated at 200° for 10 hours and poured into ice-water. The liquid separated is extracted with ether, dried over anhydrous sodium sulphate and the ether is evaporated under reduced pressure to give a red oil which is purified by silica gel column chromatography. Elution with benzene hexane (1:1) gives 2-tert-butyl-5-[N,N-dimethyl]amino-6-nitrobenzothiazole, melting at 65°-68°.

A solution of 12 g of the above compound in 350 ml of methanol is hydrogenated in presence of 40 g of Raney Nickel at ambient temperature. After removing the catalyst, the solution is concentrated and the solid filtered to yield 6-amino-2-tert-butyl-5-[N,N-dimethyl]aminobenzothiazole, melting at 169°.

To a stirred mixture of 6.7 g of the above compound and 4.1 g of dry ammonium thiocyanate in 40 ml of isopropyl alcohol at 70° is added under nitrogen, 2.7 g of concentrated sulphuric acid dropwise. The mixture is refluxed for 24 hours, cooled, poured into ice-water and the solution made alkaline with 30% sodium hydroxide solution. The solid is filtered, washed with water and isopropyl alcohol to give N-[2-tert-butyl-5-(N,N-dimethylamino)benzothiazol-6-yl]thiourea, melting at 275°-280°.

EXAMPLE 14

To a cooled mixture of 1.5 g of 6-amino-2-tert-butyl-5-[3-methylpiperidin-1-yl]benzothiazole and 1.5 g of potassium bicarbonate in 50 ml of chloroform is added dropwise 0.6 g of thiophosgene in 5 ml of chloroform under stirring. The stirring is continued for 30 minutes maintaining the temperature at 0°-2°. The solid is filtered and the filtrate is evaporated. The residue thus obtained is dissolved in chloroform and filtered through a silica gel column. The filtrate is evaporated to give 2-tert-butyl-6-isothiocyanato-5-[3-methylpiperidin-1-yl]benzothiazole, melting at 47°-52°.

The starting material is prepared as follows:

A solution of 2.7 g of 2-tert-butyl-5-chloro-6-nitrobenzothiazole described in example 5, in 25 ml of dimethyl sulfoxide is stirred and heated at 140° for 11 hours with 2.6 g of anhydrous potassium carbonate and 1 g of 3-methylpiperidine, cooled and poured into water. The material obtained is dissolved in chloroform and filtered through a silica gel column. The filtrate is evaporated to give 2-tert-butyl-5-[3-methylpiperidin-1-yl]-6-nitrobenzothiazole as an oil.

A solution of 1.7 g of 2-tert-butyl-5-[3-methylpiperidin-1-yl]-6-nitrobenzothiazole in 50 ml of methanol is hydrogenated in presence of 0.5 g of raney nickel at room temperature. After removing the catalyst the solution is concentrated and the solid filtered to give 6-amino-2-tert-butyl-5-[3-methylpiperidin-1-yl]benzothiazole melting at 108°-112°.

EXAMPLE 15

To a cooled mixture of 2.1 g of 6-amino-2-tert-butyl-5-[4-methylpiperidin-1-yl]benzothiazole and 2.6 g potassium bicarbonate in 20 ml of chloroform under stirring. The stirring is continued for 2 hours maintaining the temperature at 0°-2°. The solid is filtered and the filtrate is evaporated. The solid thus obtained is dissolved in chloroform and filtered through a silica gel column. The filtrate is evaporated to give 2-tert-butyl-6-isothiocyanato-5-[4-methylpiperidin-1-yl]benzothiazole melting at 54°-58°. The starting material is prepared as follows:

A solution of 32.4 g of 2-tert-butyl-5-chloro-6-nitrobenzothiazole described in Example 5, in 300 ml of dimethyl sulfoxide, is stirred and heated at 140° for 6 hours with 12.8 g of 4-methylpiperidine and 35.8 g of anhydrous potassium carbonate, cooled and poured into water. The solid obtained is dissolved in chloroform and filtered through a silica gel column. The filtrate is evaporated to give 2-tert-butyl-5-[4-methylpiperidin-1-yl]-6-nitrobenzothiazole melting at 116°-120°.

A solution of 15.2 g of 2-tert-butyl-5-[4-methylpiperidin-1-yl]-6-nitrobenzothiazole in 600 ml of methanol is hydrogenated in presence of 6.5 g of raney nickel at room temperature. After removing the catalyst the solution is concentrated and the solid filtered to give 6-amino-2-tert-butyl-5-[4-methylpiperidin-1-yl]benzothiazole melting at 146°-148°.

What is claimed is:

1. A benzazole compound of the formula

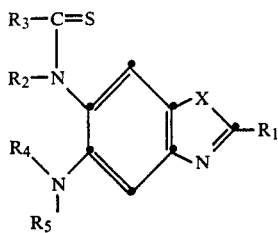

(I)

wherein
X is sulphur or oxygen;
$R_1$ is lower alkyl or lower alkenyl;
$R_2$ is hydrogen;
$R_3$ is lower alkylthio which is unsubstituted or mono subsutituted by carboxy or esterified carboxy; or $R_2$ and $R_3$ together represents a bond; and
$R_4$ and $R_5$ are hydrogen or lower alkyl; or $R_4$ and $R_5$ together with the nitrogen to which they are attached, represents a member selected from the group consisting of pyrrolidino, piperidino, hexahydroazepino, octahydroazocino, morpholino, thiamorpholino, and piperazino which is unsubstituted or substituted on carbom atoms by lower alkyl or phenyl and said piperazino is N-unsubstituted or N-substituted by a substituent selected from lower alkyl, phenyl, lower alkanoyl, benzoyl, lower alkoxycarbonyl, and lower alkane sulphonyl;
or a salt thereof.

2. A compound of claim 1 wherein
X is sulphur;
$R_1$ is lower alkyl;
$R_2$ is hydrogen;
$R_3$ is carboxy lower alkyl thio; or $R_2$ and $R_3$ together represent a bond; and
$R_4$ and $R_5$ are hydrogen or lower alkyl; or $R_4$ and $R_5$ together, with the nitrogen to which they are attached represents a member selected from the group consisting of pyrrolidino, piperidino, morpholino, thiamorpholino, and piperazino which is C-unsubstituted or C-mono or di-substituted by lower alkyl or C mono substituted by phenyl wherein said piperazino is N-unsubstituted or N-substituted by a substituent selected from lower alkyl, lower alkanoyl, lower alkoxycarbonyl, lower alkanesulphonyl, and phenyl;
or a salt thereof.

3. A compound of claim 2 wherein
X is sulphur;
$R_1$ is $C_3$-$C_4$ alkyl;
$R_2$ is hydrogen;
$R_3$ is 2-carboxylethylthio; or $R_2$ and $R_3$ together are a bond; and $R_4$ and $R_5$ are as defined in claim 2; or a pharmaceutically acceptable salt thereof.

4. A compound of claim 3 wherein
X is sulfur;
$R_1$ is tertiary-butyl;
$R_2$ and $R_3$ are as defined in claim 3; and
$R_4$ and $R_5$ are lower alkyl; or $R_4$ and $R_5$ together with the nitrogen to which they are attached represent pyrrolidyl, piperidyl, morpholinyl, piperazinyl, methyl piperidyl, methyl piperazinyl, phenyl piperazinyl, acetyl-piperazinyl, methanesulphonyl-piperazinyl, methoxycarbonyl-piperazinyl, or ethoxycarbonyl-piperazinyl;
or a pharmaceutically acceptable salt thereof.

5. A benzazole compound of the formula

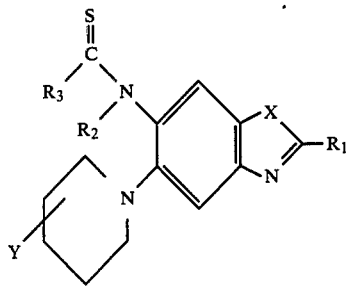

wherein
X is sulphur or oxygen;
$R_1$ is lower alkyl or lower alkenyl;
$R_2$ is hydrogen;
$R_3$ is lower alkylthio which is unsubstituted or mono substituted by carboxy or esterified carboxy; or $R_2$ and $R_3$ together represent a bond; and
Y is hydrogen, lower alkyl, or phenyl.

6. A compound as claimed in claim 4 being 2-tert-butyl-6-isothiocyanato-5-[piperidin-1-yl]benzothiazole and a therapeutically useful salt thereof.

7. A compound as claimed in claim 4 being 2-tert-butyl-6-isothiocyanato-5-[3-methylpiperidin-1-yl]benzothiazole and a therapeutically useful salt thereof.

8. A compound as claimed in claim 4 being 2-tert-butyl-6-isothiocyanato-5-[4-methylpiperidin-1-yl]benzothiazole and a therapeutically useful salt thereof.

9. A therapuetic composition for the treatment of parasitic infections by helminths comprising an effective amount of an anthelmintic active compound of formula I as claimed in claim 1 together with a pharmaceutically acceptable excipient.

10. A therapeutic composition as defined in claim 9, wherein the active compound for the control of pathogens in filariasis is 2-tert-butyl-6-isothiocyanato-5-[3-methylpiperidin-1-yl]benzothiazole.

11. A therapeutic composition as defined in claim 9, wherein the active compound for the control of pathogens in filariasis is 2-tert-butyl-6-isothiocyanato-5-[4-methylpiperidin-1-yl]benzothiazole.

12. A method for the treatment of parasitic infections by helminths which comprises administering to a living body suffering from parasitic infections an effective amount of a compound of formula I as claimed in claim 1.

* * * * *